(12) United States Patent
Chia et al.

(10) Patent No.: US 8,591,658 B2
(45) Date of Patent: Nov. 26, 2013

(54) LASER PROBE TIP FIBER CAP CLEANING

(75) Inventors: Wen-Jui Ray Chia, Sunnyvale, CA (US); Meiling Wu, San Jose, CA (US); Ming Ko, San Jose, CA (US)

(73) Assignee: AMS Research Corporation, Minnetonka, MN (US)

( * ) Notice: Subject to any disclaimer, the term of this patent is extended or adjusted under 35 U.S.C. 154(b) by 72 days.

(21) Appl. No.: 13/326,826

(22) Filed: Dec. 15, 2011

(65) Prior Publication Data
US 2012/0152275 A1 Jun. 21, 2012

Related U.S. Application Data

(60) Provisional application No. 61/423,279, filed on Dec. 15, 2010.

(51) Int. Cl.
*B08B 6/00* (2006.01)

(52) U.S. Cl.
USPC .................................. 134/1; 134/42; 65/412

(58) Field of Classification Search
USPC .................. 134/1, 42; 385/77, 78; 65/412
See application file for complete search history.

(56) References Cited

U.S. PATENT DOCUMENTS

| | | | |
|---|---|---|---|
| 5,744,090 A | | 4/1998 | Jones et al. |
| 5,906,686 A | * | 5/1999 | McNeil .............................. 134/1 |
| 2008/0193095 A1 | * | 8/2008 | Chen .............................. 385/135 |
| 2010/0135617 A1 | * | 6/2010 | Novak et al. .................... 385/77 |
| 2011/0188813 A1 | * | 8/2011 | Marcouiller et al. ........... 385/78 |

OTHER PUBLICATIONS

Douglas W. Cooper, et al., "Surface Cleaning by Electrostatic Removal of Particles," Aerosol Science and Technology, downloaded on Feb. 14, 2012, 13:1, pp. 116-123.

* cited by examiner

*Primary Examiner* — Joseph L Perrin
*Assistant Examiner* — Caitlin N Dunlap
(74) *Attorney, Agent, or Firm* — Brian D. Kaul; Westman, Champlin & Koehler, P.A.

(57) ABSTRACT

In a method of cleaning a fiber cap of a laser probe tip, a glass fiber comprising a cap body having an internal cavity and an opening to the cavity at a proximal end is provided. A particulate collecting member is also provided. An electrical charge is applied to the particulate collecting member. A distal end of the particulate collecting member is then inserted through the opening and into the cavity of the fiber cap. Particles located within the cavity are attracted to the particulate collecting member. The attracted particles attach to the particulate collecting member. The particulate collecting member is then removed from the cavity.

19 Claims, 5 Drawing Sheets

LASER PROBE TIP FIBER CAP CLEANING

CROSS-REFERENCE TO RELATED APPLICATION

The present application is based on and claims the benefit of U.S. provisional patent application Ser. No. 61/423,279, filed Dec. 15, 2010, the content of which is hereby incorporated by reference in its entirety.

FIELD

Embodiments of the invention are directed to a method of cleaning a fiber cap of a laser probe tip and, more specifically, to a method of electrostatically cleaning a fiber cap.

BACKGROUND

Medical lasers have been used in various practice areas, such as, for example, urology, neurology, otorhinolaryngology, general anesthetic ophthalmology, dentistry, gastroenterology, cardiology, gynecology, and thoracic and orthopedic procedures. Generally, these procedures require precisely controlled delivery of energy as part of the treatment protocol.

Surgical laser systems utilize a frequency doubled Nd:YAG laser, which operates at 532 nm in a quasi continuous mode at high power levels (e.g., 100 watts) and has been used to efficiently ablate tissue. The frequency doubled Nd:YAG laser can be pumped by CW krypton arc lamps and can produce a constant train of laser light pulses. When ablative power densities are used, a superficial layer of denatured tissue is left behind. At high powers, 532 nm lasers induce a superficial char layer that strongly absorbs the laser light and improves ablation efficiency.

Many surgical laser procedures utilize a surgical probe, which generally comprises an optical fiber and a fiber cap over a distal end of the optical fiber to form a probe tip. A laser source delivers laser energy through the optical fiber to the probe tip where the energy is discharged through the fiber cap and onto desired portions of the targeted tissue.

The laser energy may be directed laterally from the probe tip by reflecting the laser energy off a polished beveled surface at the distal end of the optical fiber. The fiber cap seals a cavity containing a gas (or vacuum) that maintains the necessary refractive index difference for total internal reflection at the beveled surface.

It is important that the fiber cap be free of contaminants on the walls of the interior cavity of the fiber cap that receives the distal end of the optical fiber. Such contaminates can adversely affect the assembly of the probe tip and can lead to failure of the probe tip.

SUMMARY

Embodiments of the invention are directed to a method of cleaning a fiber cap of a laser probe tip and a method of manufacturing a laser probe tip. In one embodiment of the method, a glass fiber comprising a cap body having an internal cavity and an opening to the cavity at a proximal end is provided. A particulate collecting member is also provided. An electrical charge is applied to the particulate collecting member. A distal end of the particulate collecting member is then inserted through the opening and into the cavity of the fiber cap. Particles located within the cavity are attracted to the particulate collecting member. The attracted particles attach to the particulate collecting member. The particulate collecting member is then removed from the cavity.

In one embodiment of manufacturing a laser probe tip, an optical fiber having a distal end is provided. A glass fiber cap comprising a cap body having an internal cavity and an opening to the cavity at a proximal end is provided. Particles having a first electrical charge are contained within the cavity. A particulate collecting member is also provided and an electrical charge is applied to the member. The particulate collecting member is inserted through the opening and into the cavity of the fiber cap. The particles are attracted to the member responsive to inserting the member into the cavity. The attracted particles attach to the member. The member and the attached particles are then removed from the cavity. The distal end of the optical fiber is then inserted through the opening and into the cavity of the fiber cap. The fiber cap is then attached to the distal end of the optical fiber.

Other features and benefits that characterize embodiments of the present disclosure will be apparent upon reading the following detailed description and review of the associated drawings.

DETAILED DESCRIPTION OF ILLUSTRATIVE EMBODIMENTS

Embodiments of the invention are directed to a method of cleaning a fiber cap of a laser probe tip and a method of manufacturing a laser probe tip.

Figure 1:
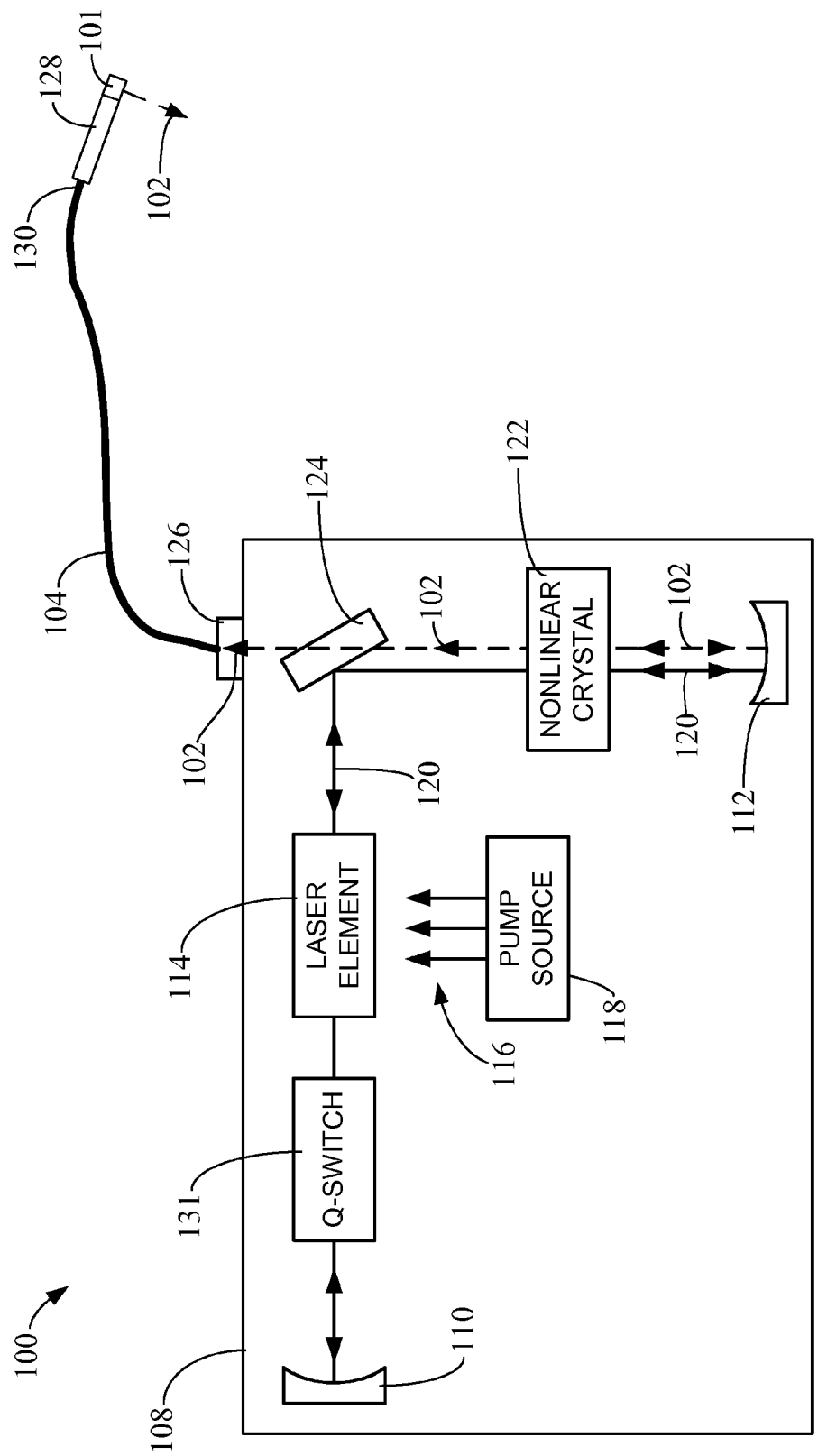
FIG. 1 is a simplified block drawing of an exemplary surgical laser system in accordance with embodiments of the invention.

FIG. 1 is a simplified diagram of an exemplary surgical laser system 100 with which a laser probe tip 101 formed in accordance with embodiments of the invention may be used. In general, the laser system 100 is configured to generate electromagnetic radiation 102 in the form of a laser beam, deliver the electromagnetic radiation through a waveguide or optical fiber 104 to the probe tip 101 where it is discharged to a desired target, such as tissue of a patient.

The exemplary system 100 comprises a laser resonator 108. The laser resonator 108 may include a first resonator minor 110, a second resonator minor 112 and a laser rod or element 114. In one embodiment, the laser element 114 comprises a yttrium-aluminum-garnet crystal rod with neodymium atoms dispersed in the YAG rod to form a Nd:YAG laser element. Other conventional laser elements 114 may also be used.

The laser element 114 is pumped by a light input 116 from an optical pump source 118, such as a Kr arc lamp or other conventional pump source, to produce laser light or beam 120 at a first frequency. The laser resonator 108 also includes a nonlinear crystal 122, such as a lithium borate (LBO) crystal or a potassium titanyl phosphate crystal (KTP), for generating a second harmonic of the laser beam 120 emitted by the laser element 114. The laser beam 120 inside the resonator 108 bounces back and forth between the first and second resonator minors 110 and 112, reflects off a folding minor 124 and propagates through the laser element 114 and nonlinear crystal 122. The laser element 114 has optical gain at a certain wavelength and this determines the wavelength of the laser beam 120 inside the resonator 108. This wavelength is also referred to as the fundamental wavelength. For the Nd:YAG laser element 114, the fundamental wavelength is 1004 nm.

A Q-switch 131 may be used in the resonator 108 to convert the laser beam 120 to a train of short pulses with high peak power. These short pulses increase the conversion efficiency of the second harmonic laser beam 102 and increase the average power of the laser beam 102 outside the resonator 108.

When the laser beam 120 inside the resonator 108 propagates through the nonlinear crystal 122 in a direction away from the folding minor 124 and toward the second resonator minor 112, a beam 102 of electromagnetic radiation at the second harmonic wavelength is output from the crystal 122. The second resonator minor 112 is highly reflective at both the fundamental and second harmonic wavelengths, and both beams 120 and 102 propagate back through the nonlinear crystal 122. On this second pass, more beams 102 at the second harmonic wavelength are produced. For example, the nonlinear crystal 122 can produce a laser beam 102 having a wavelength of approximately 532 nm (green) when a Nd:YAG rod is used as the laser element 114. One advantage of the 532 nm wavelength is that it is strongly absorbed by hemoglobin in blood and, therefore, is useful for cutting, vaporizing and coagulating vascular tissue.

The folding minor 124 is highly reflective at the fundamental wavelength and is highly transmissive at the second harmonic wavelength. Thus, the laser beam 102 at the second harmonic passes through the folding minor 124 and produces a second harmonic laser beam 102 outside the optical resonator 108. The optical fiber 104 connects to an optical coupler 126, which couples the beam 102 to the optical fiber 102. The beam 102 travels to the optical fiber 102 to a laser delivery probe 128 coupled to a distal end 130 of the optical fiber 104. In one embodiment, the probe 128 supports the optical fiber 104 and the probe tip 101 during surgical laser treatments where the beam 102 is delivered to targeted tissue of a patient through the probe tip 101. In one embodiment, the probe 128 includes an endoscope or cystoscope.

Figure 2:
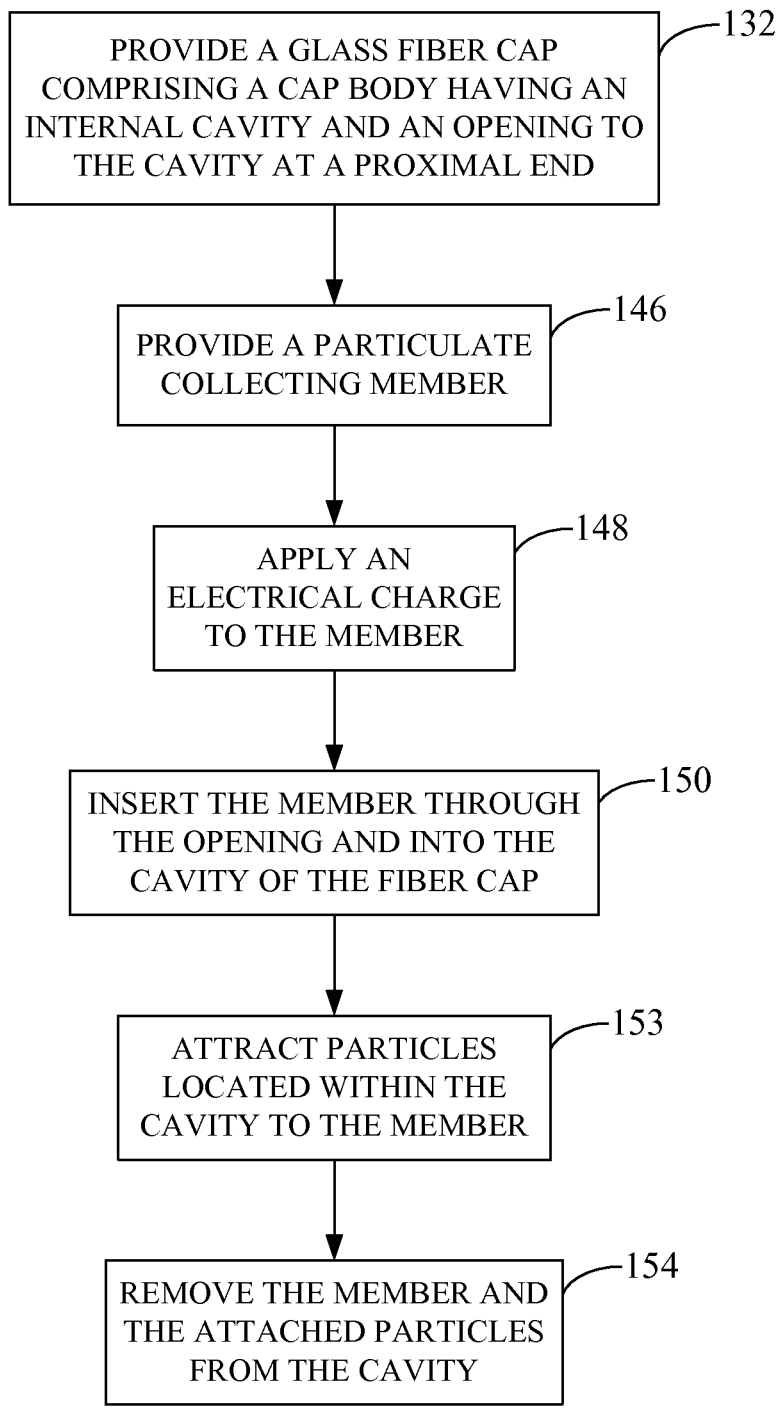
FIG. 2 is a flowchart illustrating a method of cleaning a fiber cap in accordance with embodiments of the invention.
Figure 3:
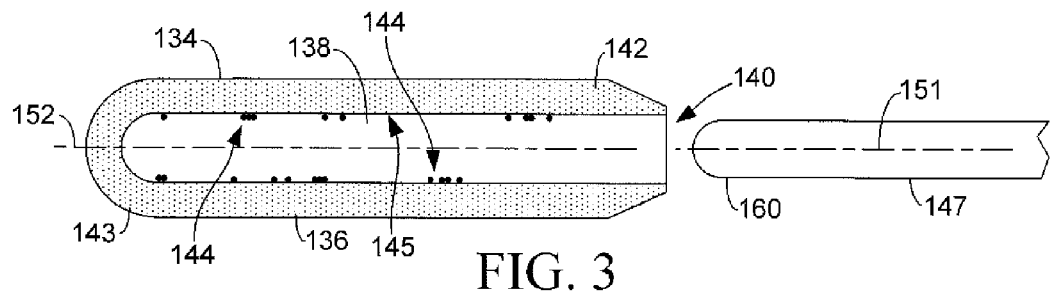
FIGS. 3-5 are simplified side cross-sectional views of a fiber cap and a particulate cleaning member illustrating steps of the fiber cap cleaning method.
Figure 4:
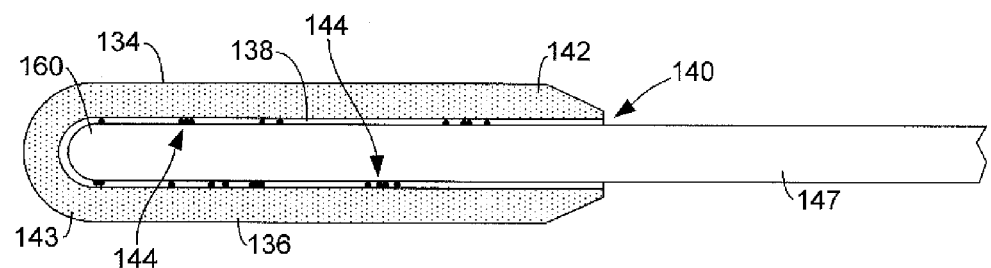
Figure 5:
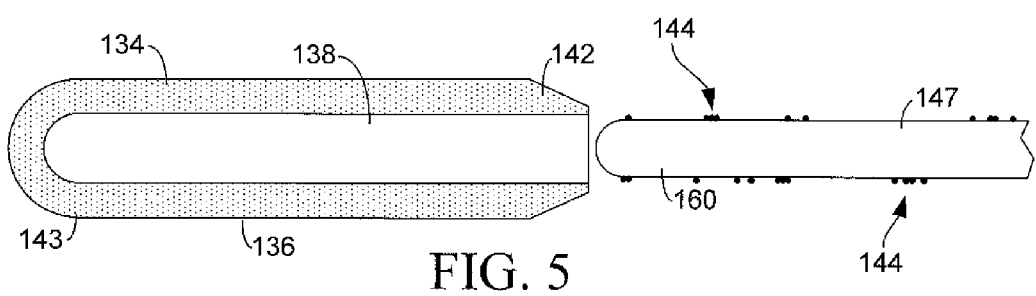

The probe tip 101 generally comprises a fiber cap that is attached to the distal end of the optical fiber 104. Embodiments of the invention are directed to methods of cleaning the fiber cap prior to its attachment to the optical fiber 104 during the manufacture of the probe tip 101. FIG. 2 is a flowchart illustrating a method of cleaning a fiber cap in accordance with embodiments of the invention. FIGS. 3-5 are simplified side cross-sectional views of steps of the fiber cap cleaning process in accordance with embodiments of the invention.

At step 132 of the method, a fiber cap 134 comprising a cap body 136 having an internal cavity 138 and an opening 140 to the cavity 138 at a proximal end 142 is provided, as shown in FIG. 3. In one embodiment, the fiber cap 134 is formed of fused silica glass. In one embodiment, the fiber cap 134 includes a cap body 136 having an interior cavity 138 and an opening 140 to the interior cavity 138 at a proximal end 142, as shown in FIG. 3. While a distal end 143 of the fiber cap 134 is illustrated as being closed, embodiments of the fiber cap 134 include an open distal end 143, which may be fused closed during manufacture of the probe tip 101.

In one embodiment, the fiber cap 134 has an electrostatic charge that attracts particles 144 within the interior cavity 138. The electrostatic charge on the fiber cap 134 generally causes the particles 144 to attach to the interior surface 145 that defines the interior cavity 138, as shown in FIG. 3. Embodiments of the invention are directed to methods of removing the particles 144 from within the interior cavity 138 of the fiber cap 134 before attaching the fiber cap 134 to the optical fiber 104.

At 146, a particulate collecting member 147 is provided. In one embodiment, the particulate collecting member 147 is in the form of an electrical insulator. Embodiments of the electrical insulator include glass, ceramic, porcelain and composite polymer materials. In one embodiment, the particulate collecting member 147 is in the form of a rod, a wire, a fiber, or woven fibers.

At 148, an electrical charge is applied to the particulate collecting member 147. In one embodiment, the electrical charge is applied to the member 147 by rubbing the particulate collecting member 147 with glass fibers or other suitable material. In accordance with another embodiment, step 148 involves applying an electrical charge to the particulate collecting member 147 using an electronic device, such as a device comprising DC power supplier or DC voltage source. The charge applied to the particulate collecting member 147 is generally identical to that typically electrostatically generated on the fiber cap 134.

At step 150 of the method, the particulate collecting member 147 is inserted through the opening 140 of the fiber cap 134 and into the cavity 138, as shown in FIG. 4. In one embodiment, the particulate collecting member 147 has a width that is slightly smaller than the opening 140 of the fiber cap 134. In one embodiment, the opening 140 has a diameter of less than 2 millimeters. In one embodiment of the inserting step 150, the distal end 160 of the particulate collecting member 147 is first aligned with the opening 140 to the fiber cap 134, such that a longitudinal axis 151 of the member 147 is generally aligned parallel with a central axis 152 of the fiber cap 134, as shown in FIG. 3. Once aligned, the distal end 160 of the particulate collecting member 147 is inserted into the cavity 138 of the fiber cap 134, as shown in FIG. 4.

At step 153 of the method, the particles 144 located within the cavity 138 of the fiber cap 134 are attracted to the particulate collecting member 147. The particles 144 are attracted to the member 147 because the particles 144 have an electrostatic charge that is opposite the electrostatic charge applied to the particulate collecting member 147 in step 148. It is also understood that the particles 144 could have a neutral charge and still be attracted to the member 147 if their charge is polarized. In one embodiment, while the electrostatic charge applied to the particulate collecting member 147 is the same polarity as the electrostatic charge on the fiber cap 134, the magnitude of electrostatic charge on the member 147 is greater than that on the fiber cap 134. As a result, the particles 144 have a greater attraction to the particulate collecting member 147 than the walls 145 of the fiber cap 134. Thus, the attracted particles 144 become attached to the particulate collecting member 147 due to the opposing electrostatic charges.

At 154, the particulate collecting member 147 is removed from the interior cavity 138 of the fiber cap 134, as shown in FIG. 5. This removal of the member 147 carries the attached particles 144 out of the fiber cap 134. Thus, embodiments of the method operate to remove the particles 144 from within the interior cavity 138 of the fiber cap 134. The fiber cap 134 cleaned of the particles 144 is ready for attachment to the distal end 130 of the optical fiber 104.

Figure 6A:
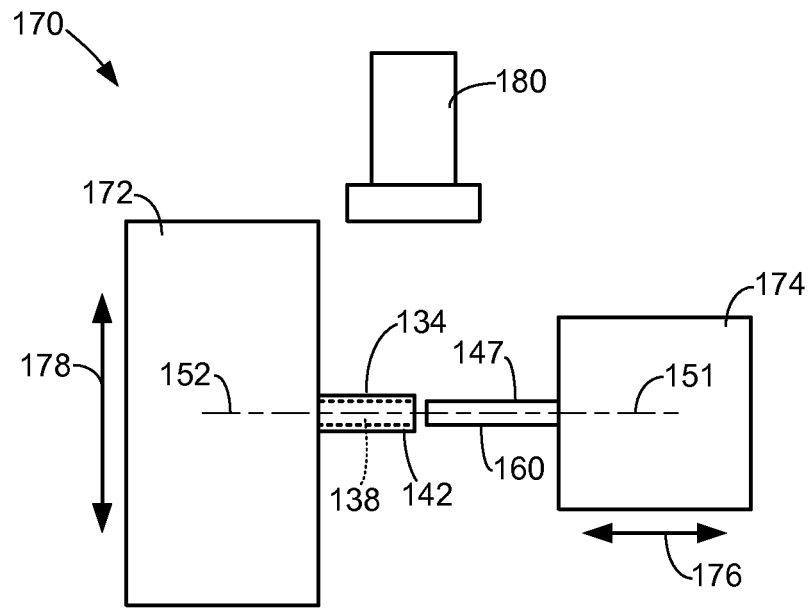
FIGS. 6A and 6B respectively are simplified top and side views of embodiments of an apparatus used to assist in the performance of method steps.
Figure 6B:
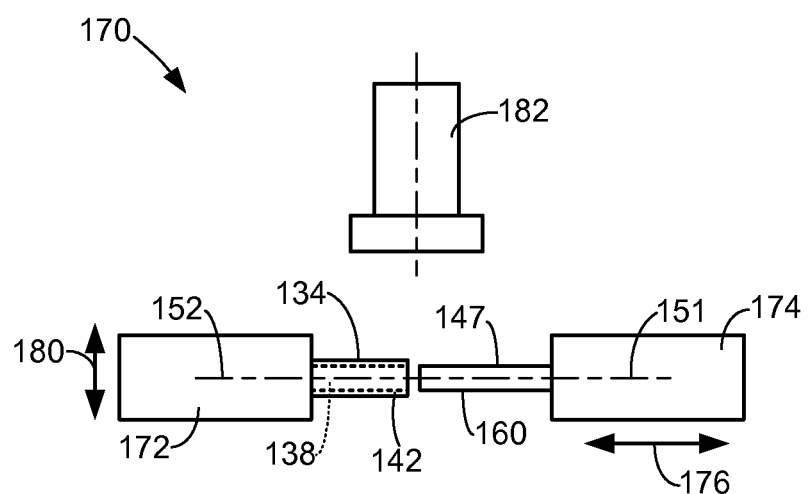

FIGS. 6A and 6B respectively are simplified top and side views of an apparatus 170 used to assist in the performance of the inserting step 150. In one embodiment, the apparatus 170 comprises a fixture 172 that supports the fiber cap 134 and a fixture 174 that supports the particulate collecting member 147. In one embodiment, the fiber cap 134 extends from the fixture 172 toward the member 147 that extends from the fixture 174. In one embodiment, the relative positions of the fixtures 172 and 174 can be adjusted along a first axis 176 that is generally aligned with the central axis 152 of the fiber cap 134 and the axis 151 of the member 147, an axis 178 that is orthogonal to the axis 176, and an axis 180 that is orthogonal to both the axes 176 and 178. The fixture 172 and/or the fixture 174 is moved along the axes 176, 178 and 180 relative to the other fixture to align the distal end 160 of the particulate collecting member 147 with the opening 140 and the longitudinal axis 151 of the member 147 with the central axis 152 of the fiber cap 134. Once aligned, the distal end 162 of the particulate collecting member 147 is then inserted into the cavity 138 of the fiber cap 134 by moving at least one of the fixtures 172 or 174 toward the other along the axis 176 to complete step 150 of the method.

Accordingly, one embodiment of the method step 150 comprises holding the fiber cap 134 in the fixture 172 and holding the particulate collecting member 147 in the fixture 174. Next, the longitudinal axis 151 of the particulate collecting member 147 is aligned with the central axis 152 of the cavity 138 of the fiber cap 134. Finally, the distal end 162 of the particulate collecting member 147 is inserted through the opening 140 and into the cavity 138 of the fiber cap 134 by moving the fixture 174 relative to the fixture 172 along the axis 176 to complete method step 150, as shown in FIG. 4.

In one embodiment, the apparatus 170 includes a pair of cameras 180 (FIG. 6A) and 182 (FIG. 6B) that assist in aligning the distal end 160 of the particulate collecting member 147 with the opening 140. In one embodiment, the camera 180 is positioned to provide a magnified view of the proximal end 142 of the fiber cap 134 and the distal end 160 of the particulate collecting member 147 along the direction of the axis 178. The camera 182 is configured to provide a user with a magnified view of the proximal end 142 of the fiber cap 134 and the distal end 162 of the particulate collecting member 147 in the direction of the axis 180. The views from the cameras 180 and 182 are preferably provided on one or more displays (not shown) for the user.

While viewing the images produced by the cameras 180 and 182, a user can adjust the relative positions of the fixtures 172 and 174 along the axes 176, 178 and 180 to align the particulate collecting member 147 to the fiber cap 134. Once the member 147 is properly aligned, the fixtures 172 and 174 are moved relative to each other along the axis 176 to insert the distal end 162 of the particulate collecting member 147 into the cavity 138 of the fiber cap 134 to complete the method step 150, as shown in FIG. 4.

Figure 7:
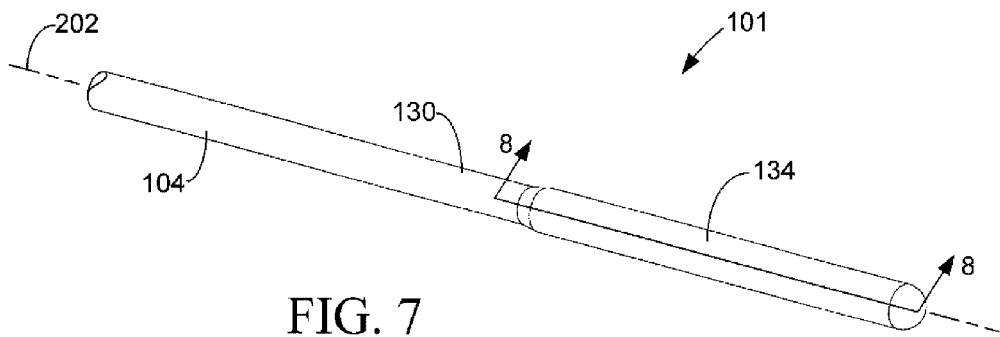
FIG. 7 is an isometric view of an exemplary probe tip in accordance with embodiments of the invention.
Figure 8:
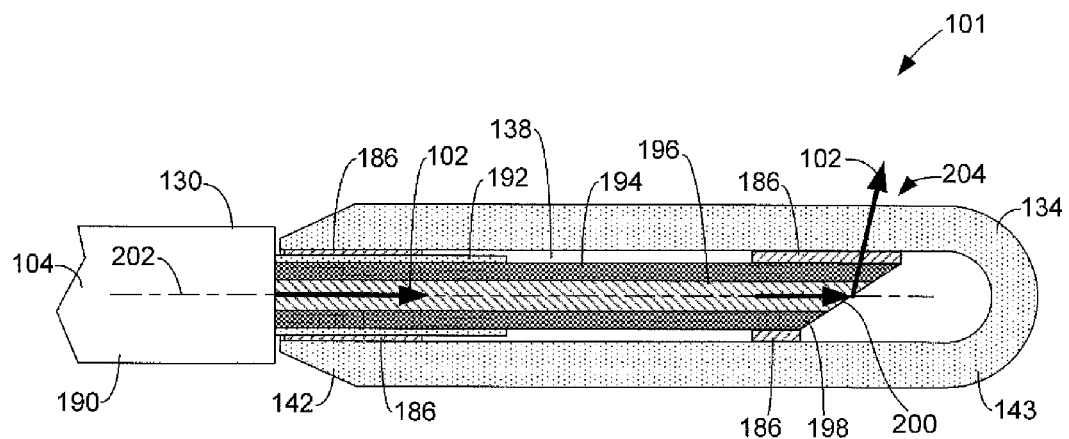
FIG. 8 is a side cross-sectional view of the exemplary probe tip of FIG. 7 taken generally along line 8-8.

The removal of the particles 144 from the interior cavity 138 of the fiber cap 134 prepares the fiber cap 134 for attachment to the distal end 130 of the optical fiber 104, as shown in the isometric view of an exemplary probe tip 101 provided in FIG. 7. FIG. 8 is a side cross-sectional view of the exemplary probe tip 101 shown in FIG. 7 taken generally along line 8-8.

The exemplary optical fiber 104 shown in FIG. 8 generally comprises a nylon jacket 190, a buffer or hard cladding 192, cladding 194 and an optical fiber core 196. It is understood that other forms of optical fibers may also be used. The optical fiber core 196 operates as a waveguide through which the electromagnetic energy 102 travels. In one embodiment, the nylon jacket 190 and at least a portion of the hard cladding 192 are removed from the distal end 130 of the optical fiber 104 to expose the cladding 194 before attaching the fiber cap 134, as shown in FIG. 8. In one embodiment, the fiber cap 134 is attached to the optical fiber 104 by fusing the fiber cap 134 to the optical fiber 104. In one embodiment, the fiber cap 134 is fused to the hard cladding 192 and/or the cladding 194, as represented by element 186 in FIG. 8. In one embodiment, the fiber cap 134 is adhered to the optical fiber 104 using a suitable adhesive.

A distal tip 198 of the optical fiber core 196 may be formed to output the electromagnetic energy 102 as desired in accordance with conventional designs. For example, the distal tip 198 may comprise a polished beveled surface 200 that is non-perpendicular to a longitudinal axis 202 of the optical fiber core 196. The beveled surface 200 operates to reflect the laser light 102 laterally through a transmitting surface 204 of the fiber cap 134, as shown in FIG. 8.

Although the present invention has been described with reference to preferred embodiments, workers skilled in the art will recognize that changes may be made in form and detail without departing from the spirit and scope of the invention.

What is claimed is:

1. A method of cleaning a fiber cap configured to be coupled to a distal end of an optical fiber to form a laser probe tip, the method comprising:
   providing a glass fiber cap comprising a cap body having an internal cavity and an opening to the cavity at a proximal end;
   providing a particulate collecting member;
   applying an electrical charge to the particulate collecting member;
   inserting a distal end of the particulate collecting member through the opening and into the cavity of the fiber cap;
   attracting particles located within the cavity to the particulate collecting member, wherein the attracted particles attach to the particulate collecting member; and
   removing the particulate collecting member and the attached particles from the cavity.

2. The method of claim 1, wherein providing a particulate collecting member comprises providing a particulate collecting member comprising an electrical insulator selected from the group consisting of glass, ceramic, porcelain and composite polymer materials.

3. The method of claim 2, wherein providing a particulate collecting member comprises providing a particulate collecting member in the form of a rod, a wire, or a fiber.

4. The method of claim 1, wherein applying an electrical charge to the member comprises rubbing the member with glass fibers or charging the member with an electronic device.

5. The method of claim 1, wherein inserting a distal end of the particulate collecting member through the opening and into the cavity of the fiber cap comprises:
   holding the fiber cap in a first fixture;
   holding the particulate collecting member in a second fixture;
   aligning a longitudinal axis of the member to a central axis of the cavity of the fiber cap; and
   inserting the member through the opening and into the cavity of the fiber cap.

6. The method of claim 5, wherein aligning a longitudinal axis of the member to a central axis of the cavity of the fiber cap comprises viewing the fiber cap and the member from two substantially orthogonal angles that are each substantially orthogonal to the longitudinal axis of the member and the central axis of the cavity.

7. The method of claim 6, wherein aligning a longitudinal axis of the member to a central axis of the cavity of the fiber cap comprises adjusting the relative positions of the first and second fixtures.

8. The method of claim 5, wherein inserting a distal end of the particulate collecting member into the cavity of the fiber cap comprises moving the second fixture relative to the first fixture along the central axis of the member.

9. The method of claim 1, wherein:
the particles have a first electrical charge;
applying an electrical charge to the member comprises applying a second electrical charge to the member that is opposite the first electrical charge; and
attracting particles located within the cavity to the member comprises electrostatically attracting the particles to the member.

10. A method of manufacturing a laser probe tip comprising:
providing an optical fiber having a distal end;
providing a glass fiber cap comprising a cap body having an internal cavity and an opening to the cavity at a proximal end, wherein particles are contained within the cavity;
providing a particulate collecting member;
applying an electrical charge to the member;
inserting the member through the opening and into the cavity of the fiber cap;
attracting the particles to the member responsive to inserting the member into the cavity, wherein the attracted particles attach to the member;
removing the member and the attached particles from the cavity;
inserting the distal end of the optical fiber through the opening and into the cavity; and
attaching the fiber cap to the distal end of the optical fiber.

11. The method of claim 10, wherein providing a particulate collecting member comprises providing a particulate collecting member comprising an electrical insulator selected from the group consisting of glass, ceramic, porcelain and composite polymer materials.

12. The method of claim 11, wherein providing a particulate collecting member comprises providing a particulate collecting member in the form of a rod, a wire, or a fiber.

13. The method of claim 10, wherein applying electrical charge to the member comprises rubbing the member or charging the member with an electronic device.

14. The method of claim 10, wherein inserting the member into the cavity of the cap comprises:
holding the fiber cap in a first fixture;
holding the particulate collecting member in a second fixture;
aligning a longitudinal axis of the member to a central axis of the cavity of the fiber cap; and
inserting the member through the opening and into the cavity of the fiber cap.

15. The method of claim 14, wherein aligning a longitudinal axis of the member to a central axis of the cavity of the fiber cap comprises viewing the fiber cap and the member from two substantially orthogonal angles that are each substantially orthogonal to the longitudinal axis of the glass member and the central axis of the cavity.

16. The method of claim 15, wherein aligning a longitudinal axis of the member to a central axis of the cavity of the fiber cap comprises adjusting the relative positions of the first and second fixtures.

17. The method of claim 14, wherein inserting the member into the cavity of the fiber cap comprises moving the second fixture relative to the first fixture along the central axis of the member.

18. The method of claim 10, wherein:
the particles have a first electrical charge;
applying an electrical charge to the member comprises applying a second electrical charge to the member that is opposite the first electrical charge; and
attracting particles located within the cavity to the member comprises electrostatically attracting the particles to the member.

19. The method of claim 10, wherein attaching the fiber cap to the distal end of the optical fiber comprises one of fusing the fiber cap to the optical fiber and adhering the fiber cap to the optical fiber.

* * * * *